(12) United States Patent  
Dukart et al.

(10) Patent No.: US 8,791,097 B2  
(45) Date of Patent: Jul. 29, 2014

(54) ANTI-TUMOR ACTIVITY OF CCI-779 IN PAPILLARY RENAL CELL CANCER

(75) Inventors: Gary Dukart, Ambler, PA (US); James Joseph Gibbons, Jr., Westwood, NJ (US); Anna Berkenblit, Needham, MA (US); Jay Marshall Feingold, Wynnewood, PA (US)

(73) Assignee: Wyeth LLC, New York, NY (US)

( * ) Notice: Subject to any disclaimer, the term of this patent is extended or adjusted under 35 U.S.C. 154(b) by 1493 days.

(21) Appl. No.: 12/099,394

(22) Filed: Apr. 8, 2008

(65) Prior Publication Data

US 2008/0255177 A1    Oct. 16, 2008

Related U.S. Application Data

(60) Provisional application No. 60/922,759, filed on Apr. 10, 2007.

(51) Int. Cl.
*A01N 43/00*    (2006.01)
*A61K 31/33*    (2006.01)
*A01N 43/42*    (2006.01)
*A61K 31/44*    (2006.01)
*A61K 31/436*   (2006.01)

(52) U.S. Cl.
CPC .................................. *A61K 31/436* (2013.01)
USPC .......................................... 514/183; 514/291

(58) Field of Classification Search
USPC ................................................ 514/183, 291
See application file for complete search history.

(56) References Cited

U.S. PATENT DOCUMENTS

| | | | |
|---|---|---|---|
| 5,362,718 A | 11/1994 | Skotnicki et al. |
| 5,665,772 A | 9/1997 | Cottens et al. |
| 6,277,983 B1 | 8/2001 | Shaw et al. |
| 6,617,333 B2 | 9/2003 | Rabindran et al. |
| 7,189,735 B2 | 3/2007 | Dukart et al. |
| 2004/0077677 A1 | 4/2004 | Ashraf et al. |
| 2004/0167152 A1 | 8/2004 | Rubino et al. |
| 2004/0176339 A1 | 9/2004 | Sherman et al. |
| 2004/0258662 A1 | 12/2004 | Gibbons et al. |
| 2005/0033046 A1 | 2/2005 | Chew et al. |
| 2005/0187184 A1 | 8/2005 | Gibbons et al. |
| 2005/0272758 A1 | 12/2005 | Bayever et al. |
| 2006/0030547 A1 | 2/2006 | Dukart et al. |
| 2006/0035904 A1 | 2/2006 | Frisch et al. |
| 2007/0142425 A1 | 6/2007 | Dukart et al. |

FOREIGN PATENT DOCUMENTS

| | | |
|---|---|---|
| WO | WO 2004/093854 | 11/2004 |
| WO | WO 2004/097052 | 11/2004 |

OTHER PUBLICATIONS

Motzer et al. Journal of Clinical Oncology, vol. 20, No. 9, 2002, pp. 2376-2381.*

Amato, R.J., "Renal cell carcinoma: review of novel single-agent therapeutics and combination regimens," *Ann. Oncol.*, 16(1):7-15 (Jan. 2005).

Atkins, et al., "Randomized phase II study of multiple dose levels of CCI-779, a novel mammalian target of rapamycin kinase inhibitor, in patients with advanced refractory renal cell carcinoma," *J. Clin. Oncol.*, 22(5):909-918 (Mar. 1, 2004).

Dutcher, et al., "Preliminary report of a phase 1 study of intravenous (IV) CCi-779 given in combination with interferon-α (IFN) to patients with advanced renal cell carcinoma (RCC)," *Proc. Am. Soc. Clin. Oncol.*, 22: Abst 854 (2003).

Hidalgo, et al., "Phase I and pharmacological studies with the rapamycin analog CCI-779 administered as a 30 minute IV infusion," *NCI CTEP Drug Development Meeting*, (1999).

Hidalgo, et al., "A phase I and pharmacological study of CCI-779, a rapamycin ester cell cycle inhibitor," *Ann. Oncol.*, 11(S.4): 133 (Oct. 2000).

Hidalgo, et al., "The rapamycin-sensitive signal transduction pathway as a target for cancer therapy," *Oncogene*, 19(56): 6680-6686 (Dec. 27, 2000).

Hidalgo, et al., "CCI-779, a rapamycin analog and multifaceted inhibitor of signal transduction: a phase I study," *Proc. Am. Soc. Clin. Oncol.*, 19: Abst. 26 (2000).

Hidalgo, et al., "Phase I and pharmacological study of CCI-779, a cell cycle inhibitor," *Proc. 11th NCI EORTC AACR Symposium*, Abst. 413 (2000).

Hidalgo, et al., "A phase I and pharmacokinetic study of temsirolimus (CCI-779) administered intravenously daily for 5 days every 2 weeks to patients with advanced cancer," *Clin. Cancer Res.*, 12(19):5755-5763 (Oct. 1, 2006).

Hidalgo, et al., "A randomized double-blind phase 2 study of intravenous (IV) CCI-779 administered weekly to patients with advanced renal cell carcinoma (RCC): prognostic factor analysis," *Proc. Am. Soc. Clin. Oncol.*, 22: Abst. 804 (2003).

Hudes, et al., "A phase 3, randomized, 3-arm study of temsirolimus (TEMSR) or interferon-alpha (IFN) or the combination of TEMSR + IFN in the treatment of first-line, poor-risk patients with advanced renal cell carcinoma(adv RCC)," *J. Clin. Oncol.*, 24(18S):LBA4 (Jun. 20, 2006).

Hudes, et al., "Temsirolimus, interferon alfa, or both for advanced renal-cell carcinoma," *N. Engl. J. Med.*, 356(22):2271-2281 (May 31, 2007).

Raymond, et al., Safety and pharmacokinetics of escalated doses of weekly intravenous infusion of CCI-779, a novel mTOR inhibitor, in patients with cancer, *J. Clin. Oncol.*, 22(12):2336-2347 (Jun. 15, 2004; E-pub May 10, 2004).

Smith, et al., "Update of phase 1 study of intravenous CCI-779 given in combination with interferon-α to patients with advanced renal cell carcinoma," *J. Clin. Oncol.*, 22(14S):4513 (Jul. 15, 2004).

Yang, et al., "A molecular classification of papillary renal cell carcinoma," *Cancer Res.*, 65(13): 5628-5637 (Jul. 1, 2005).

Yu, et al., "mTOR, a novel target in breast cancer: the effect of CCI-779, an mTOR inhibitor, in preclinical models of breast cancer," *Endoc. Relat. Cancer*, 8(3):249-258 (Sep. 2001).

(Continued)

*Primary Examiner* — Samira Jean-Louis  
(74) *Attorney, Agent, or Firm* — David Rubin

(57) ABSTRACT

This invention provides the method or use of CCI-779 in the treatment of papillary renal cell carcinoma.

14 Claims, No Drawings

(56) References Cited

OTHER PUBLICATIONS

Nexavar® sorafenib (tablets, oral) Full Prescribing Information, http://berlex.bayerhealthcare.com/html/products/pi/Nexavar_PI.pdf, Revised Jan. 2008 (Initial U.S. Approval: 2005).

Sutent® sunitinib malate (capsules, oral) Full Prescribing Information, http://www.pfizer.com/files/products/uspi_sutent.pdf, Revised May 2008 (Initial U.S. Approval: 2006).

Dutcher, et al., "Correlation of Survival with Tumor Histology, Age, and Prognostic Risk Group for Previously Untreated Patients with Advanced Renal Cell Carcinoma (adv RCC) Receiving Temsirolimus (TEMSR) or Interferone-Alpha (INF)", *Journal of Clinical Oncology & ASCO Annual Meeting Proceedings*, 25(18S): 5033, XP002489424, (Jun. 2007).

Schrader, et al., "Metastatic Non-Clear Cell Renal Cell Carcinoma: Current Therapeutic Options", *BJU International*, 101(11): 1343-1345, XP002489425, (Jun. 2008).

International Search Report dated Aug. 7, 2008 in corresponding PCT Application No. PCT/US2008/004501.

\* cited by examiner

ANTI-TUMOR ACTIVITY OF CCI-779 IN PAPILLARY RENAL CELL CANCER

CROSS-REFERENCE TO RELATED APPLICATIONS

This application claims the benefit under 35 USC 119(e) of prior U.S. Provisional Patent Application No. 60/922,759, filed Apr. 10, 2007.

BACKGROUND OF THE INVENTION

CCI-779 is rapamycin 42-ester with 3-hydroxy-2-(hydroxymethyl)-2-methylpropionic acid, an ester of rapamycin which has demonstrated significant inhibitory effects on tumor growth in both in vitro and in vivo models. This compound is now known generically under the name temsirolimus. The use of CCI-779 alone [see, e.g., U.S. Pat. No. 7,189,735] or in combination with other active agents [see, e.g., US Published Patent Application No. 2004-0258662 A1] has been described.

Renal cell carcinoma (RCC) is the most common primary renal malignant neoplasm in adults, accounting for more than 85% of all malignant kidney tumors and 2% of all adult malignancies. The majority of renal tumor malignancies arises from the tubular epithelium and is divided into several distinct subtypes based on morphologic features defined in the WHO International Histological Classification of Kidney Tumors.

The most common subtype, clear-cell renal cell carcinoma (cRCC) accounts for approximately 70-75% of all RCCs. Papillary renal cell carcinoma (pRCC) is the second most common subtype with ~15% of cases, followed by chromophobe (~5%), oncocytoma (~3%), and collecting duct (~2%).

PRCC is histologically characterized by the presence fibrovascular cores with tumor cells arranged in a papillary configuration. The majority of PRCC tumors show indolent behavior and have a limited risk of progression and mortality, but a distinct subset displays highly aggressive behavior [X. J. Yang et al, *Cancer Res.* 65, 5628 (2005)]. Treatment of PRCC has remained problematic. To date, no effective therapy is available for patients with advanced pRCC and patients with pRCC are usually excluded from clinical trials that are usually designed for the more common clear cell renal cell carcinoma.

Multi-kinase inhibitors, Sorafenib (Nexavar™) and Sunitinib (Sutent™), have gained FDA approval for treatment of patients with advanced renal cell carcinoma and metastatic kidney cancer. Both inhibitors are small molecule multi-receptor kinase inhibitors of VEGF, PDGFR, and others and have demonstrated improved progression-free survival with a decreased toxicity profiles compared to some of the conventional cytokine therapies. However, these clinical trials enrolled only patients with clear-cell pathology and excluded patients having non-clear cell pathology.

What are needed are effective methods for treating non-clear cell renal cell cancers.

SUMMARY OF THE INVENTION

The present invention provides a method for treating non-clear cell renal cell cancers, for example papillary renal cell carcinoma, using an mTOR inhibitor, for example CCI-779 (temsirolimus).

The present invention also provides the use of an mTOR inhibitor, for example CCI-779 (temsirolimus), for treating, or in the manufacture of a medicament for treating, non-clear cell renal cell cancers, for example papillary renal cell carcinoma.

In one aspect, the invention provides a method of treating papillary renal cell carcinoma in a subject in need thereof by administration of an effective amount of CCI-779 as the sole anti-neoplastic agent. In one embodiment, the subject previously untreated by any systemic anti-neoplastic agent.

In a further aspect, the invention provides for the use of CCI-779 for treating hereditary type I papillary renal cell carcinoma. In yet a further aspect, the invention provides for the use of CCI-779 in treating hereditary type II papillary renal cell carcinoma. In still another aspect, the invention provides for the use of CCI-779 in treating sporadic papillary renal cell carcinoma.

Still other aspects and advantages of the invention will be apparent from the following detailed description of the invention.

DETAILED DESCRIPTION OF THE INVENTION

This invention provides for the use of a rapamycin derivative, CCI-779, in treating, or preparing a medicament for treating, papillary renal cell carcinoma in a subject, for example for treating hereditary type I pRCC, hereditary type II pRCC, including sporadic pRCC, and including pRCC which is previously untreated, refractory, or advanced.

As used in accordance with this invention, the term "treating" means treating a mammal having papillary renal cell neoplasms by providing said mammal an effective amount of CCI-779 with the purpose of reducing or eradicating the neoplasms and/or prolonging survival of the mammal and/or palliation of the mammal.

As used herein, papillary renal cell carcinoma can be further classified into subtypes 1 and 2, and may be present as mixtures of these subtypes. Type 1 is characterized as consisting of papillae and tubular structures covered by small cells with pale cytoplasm, small oval nuclei with inconspicuous nucleoli, frequent glomeruloid papillae, papillary edema, foamy macrophages in papillary cores, and psammoma bodies. Type 2 is characterized as consisting of papillae covered by large cells with abundant eosinophilic cytoplasm and pseudostratification. PRCC can also occur in both sporadic (non-hereditary) and hereditary forms.

As used in accordance with this invention, the term "providing," with respect to providing CCI-779, means either directly administering CCI-779, or administering a prodrug, derivative, or analog which will form an effective amount of CCI-779 within the body.

As used in accordance with this invention, the term "previously untreated" refers to neoplasms in patients that have not been treated with standard, systemic, chemotherapy or other approved or experimental treatments appropriate for that given neoplasm.

As used in accordance with this invention, the term "refractory" refers to neoplasms in patients which typically had progressed following treatment with standard chemotherapy that was appropriate for that given neoplasm.

As used herein, the term a CCI-779 means rapamycin 42-ester with 3-hydroxy-2-(hydroxymethyl)-2-methylpropionic acid (temsirolimus), and encompasses prodrugs, derivatives, pharmaceutically acceptable salts, or analogs thereof. The terms "CCI-779" and "temsirolimus" are used interchangeably throughout this specification.

The preparation of temsirolimus is described in U.S. Pat. No. 5,362,718. A regiospecific synthesis of temsirolimus is described in U.S. Pat. No. 6,277,983, which is hereby incorporated by reference. Still another regiospecific method for synthesis of temsirolimus is described in U.S. patent application Ser. No. 10/903,062, filed Jul. 30, 2004 [published as US Patent Publication No. 2005-0033046-A1 on Feb. 10, 2005], and its counterpart, International Patent Publication No. WO 2005/016935 (published Apr. 7, 2005).

In one embodiment, temsirolimus is provided in the treatment of hereditary type I papillary renal cell carcinoma. In another embodiment, temsirolimus is provided in the treatment of hereditary type II papillary renal cell carcinoma. In still another embodiment, temsirolimus is provided in the treatment of sporadic papillary renal cell carcinoma. In still another embodiment, the papillary renal cell carcinoma is previously untreated. In another embodiment, the papillary renal cell carcinoma is advanced.

In another aspect, the papillary renal cell carcinoma is associated with poor-risk features, i.e., prognostic factors for shortened patient survival. In further embodiments, the poor-risk features include: elevated serum lactate dehydrogenase levels; reduced hemoglobin levels; elevated serum calcium; time from initial diagnosis to randomization less than one year; a Karnofsky performance score of 70 or below; and multiple organ sites of metastases.

In one embodiment, temsirolimus is administered as the sole active agent, e.g., excluding chemotherapeutic agents, such as alkylating agents; hormonal agents (i.e., estramustine, tamoxifen, toremifene, anastrozole, or letrozole); antibiotics (i.e., plicamycin, bleomycin, mitoxantrone, idarubicin, dactinomycin, mitomycin, or daunorubicin); antimitotic agents (i.e., vinblastine, vincristine, teniposide, or vinorelbine); topoisomerase inhibitors (i.e., topotecan, irinotecan, etoposide, or doxorubicin); and other agents (i.e., hydroxyurea, trastuzumab, altretamine, rituximab, paclitaxel, docetaxel, L-asparaginase, or gemtuzumab ozogamicin); biochemical modulating agents, imatib, EGFR inhibitors such as EKB or other multi-kinase inhibitors, e.g., those that targets serine/threonine and receptor tyrosine kinases in both the tumor cell and tumor vasculature, or immunomodulators (i.e., interferons, IL-2, or BCG). Examples of interferons include interferon a (alpha interferon), interferon β, interferon γ, and mixtures thereof.

In another embodiment, CCI-779 is the sole anti-neoplastic agent. In still another embodiment, CCI-779 is provided with a further active agent, provided that the further active agent is not an interferon, for example alpha interferon.

As is typical with oncology treatments, dosage regimens are closely monitored by the treating physician, based on numerous factors including the severity of the disease, response to the disease, any treatment related toxicities, age, and health of the patient. It is projected that initial i.v. infusion dosages of the temsirolimus will be from about 1 to 250 mg, about 5 to about 175 mg, or about 5 to about 25 mg, when administered on a weekly dosage regimen. In one embodiment, the dosage is 1 to 250 mg per week. In a further embodiment, the dosage is 25 mg per week. Other dosage regimens and variations are foreseeable, and will be determined through physician guidance. It is preferred that the temsirolimus is administered by i.v. infusion or orally, preferably in the form of tablets or capsules. In one embodiment, administration is weekly for from one to 24 months. However, other periods of treatment are appropriate and are within the skill in the art.

Dosage regimens are expected to vary according to the route of administration. It is projected that the oral dosage of the temsirolimus useful in the invention will be 10 mg/week to 250 mg/week, about 20 mg/week to about 150 mg/week, about 25 mg/week to about 100 mg/week, or about 30 mg/week to about 75 mg/week. For rapamycin, the projected oral dosage will be between 0.1 mg/day to 25 mg/day. Precise dosages will be determined by the administering physician based on experience with the individual subject to be treated.

Oral formulations containing the temsirolimus useful in this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed. Preferred oral formulations for rapamycin 42-ester with 3-hydroxy-2-(hydroxymethyl)-2-methylpropionic acid are described in US Patent Publication No. 2004/0077677 A1, published Apr. 22, 2004.

In some cases it may be desirable to administer a temsirolimus composition directly to the airways in the form of an aerosol.

A temsirolimus composition may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Preferred injectable formulations for rapamycin 42-ester with 3-hydroxy-2-(hydroxymethyl)-2-methylpropionic acid are described in US Patent Publication No. 2004/0167152 A1, published Aug. 26, 2004.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

In one embodiment, another mTOR inhibitor may be substituted for the temsirolimus in a method or composition used in the method of the invention. As used herein, the term mTOR inhibitor means a compound or ligand, or a pharmaceutically acceptable salt thereof, that inhibits cell replication by blocking the progression of the cell cycle from G1 to S. The term includes the neutral tricyclic compound rapamycin (sirolimus) and other rapamycin compounds, including, e.g., rapamycin derivatives, rapamycin analogues, other macrolide compounds that inhibit mTOR activity, and all compounds included within the definition below of the term "a rapamycin". These include compounds with a structural similarity to "a rapamycin", e.g., compounds with a similar macrocyclic structure that have been modified to enhance therapeutic benefit. FK-506 can also be used in the method of the invention.

As used herein, the term a rapamycin defines a class of immunosuppressive compounds that contain the basic rapamycin nucleus as shown below.

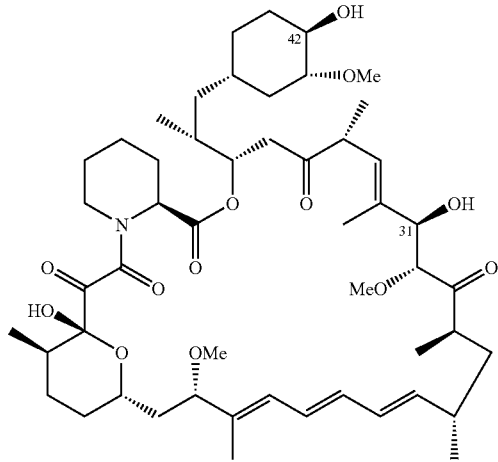 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

The rapamycins of this invention include compounds that are chemically or biologically modified as derivatives of the rapamycin nucleus, while still retaining immunosuppressive properties. Accordingly, the term a rapamycin includes rapamycin, and esters, carbamates, oximes, hydrazones, and hydroxylamines of rapamycin, as well as rapamycins in which functional groups on the rapamycin nucleus have been modified, for example through reduction or oxidation. Also included in the term a rapamycin are pharmaceutically acceptable salts of rapamycins.

The term a rapamycin also includes 42- and/or 31-esters and ethers of rapamycin as described in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl esters (U.S. Pat. No. 5,120,842); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers is disclosed in the patents listed above.

Further included within the definition of the term a rapamycin are 27-esters and ethers of rapamycin, which are disclosed in U.S. Pat. No. 5,256,790. Also described are C-27 ketone rapamycins which are reduced to the corresponding alcohol, which is in turn converted to the corresponding ester or ether. The preparation of these esters and ethers is disclosed in the patent listed above. Also included are oximes, hydrazones, and hydroxylamines of rapamycin are disclosed in U.S. Pat. Nos. 5,373,014, 5,378,836, 5,023,264, and 5,563,145. The preparation of these oximes, hydrazones, and hydroxylamines is disclosed in the above-listed patents. The preparation of 42-oxorapamycin is disclosed in U.S. Pat. No. 5,023,263.

Examples of a rapamycin include, e.g., rapamycin, 32-deoxorapamycin, 16-pent-2-ynyloxy-32-deoxorapamycin, 16-pent-2-ylyloxy-32(S)-dihydro-rapamycin, 16-pent-2-ylyloxy-32(S)-dihydr-o-40-O-(2-hydroxyethyl)-rapamycin, 40-O-(2-hydroxyethyl)-rapamycin, rapamycin 42-ester with 3-hydroxy-2-(hydroxymethyl)-2-methylpropionic acid (CCI-779), 40-[3-hydroxy-2-(hydroxymethyl)-2-meth-yl-propanoate]-rapamycin, or a pharmaceutically acceptable salt thereof, as disclosed in U.S. Pat. No. 5,362,718, ABT578, or 40-(tetrazolyl)-rapamycin, 40-epi-(tetrazolyl)-rapamycin, e.g., as disclosed in International Patent Publication No. WO 99/15530, or rapamycin analogs as disclosed in International Patent Publication No. WO 98/02441 and WO 01/14387, e.g., AP23573. In another embodiment, the compound is Certican™ (everolimus, 2-O-(2-hydroxy)ethyl rapamycin, Novartis, U.S. Pat. No. 5,665,772).

The following standard pharmacological test procedure can be used to determine whether a compound is an mTOR inhibitor, as defined herein. Treatment of growth factor stimulated cells with an mTOR inhibitor like rapamycin completely blocks phosphorylation of serine 389 as evidenced by Western blot and as such constitutes a good assay for mTOR inhibition. Thus, whole cell lysates from cells stimulated by a growth factor (e.g. IGF1) in culture in the presence of an mTOR inhibitor should fail to show a band on an acrylamide gel capable of being labeled with an antibody specific for serine 389 of p70s6K.

In one embodiment, a method of treating papillary renal cell carcinoma in a mammal in need thereof is provided, which comprises providing to said mammal an effective amount of CCI-779 in the absence of interferon alpha (α-interferon or α-IFN). Also provided is the use of CCI-779 in a medicament for treatment regimen for papillary renal cell carcinoma in a mammal in need thereof, wherein CCI-779 is the sole active agent in the regimen. In still another embodiment, provided is the use of CCI-779 in a medicament for treatment regimen for papillary renal cell carcinoma in a mammal in need thereof, wherein CCI-779 is in a combination regimen, wherein said regimen excludes alpha interferon.

In a further aspect, the invention includes a product or pharmaceutical pack containing a course of an anti-neoplastic treatment for one individual mammal comprising one or more container(s) having one, one to four, or more unit(s) of temsirolimus in unit dosage form. In another embodiment, pharmaceutical packs contain a course of anti-neoplastic treatment for one individual mammal comprising a container having a unit of a temsirolimus in unit dosage form.

In some embodiments, the compositions of the invention are in packs or kits in a form ready for administration. In other embodiments, the compositions of the invention are in concentrated form in packs, optionally with the diluent required to make a final solution for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

The following examples are illustrative of the present invention, but are not a limitation thereof.

Example

CCI-779 as a Sole Systemic Active Agent Against Non-Clear Cell Renal Cell Carcinoma In this phase III study, 626 advanced metastatic renal cell carcinoma patients from 26 countries were randomized to αIFN or CCI-779 (temsirolimus) as first-line therapy. This group is a very poor prognosis group of patients with many risk factors for early death. Patients received 3 million units (MU) of αIFN-alone subcutaneously 3 times/week, escalating to 18 MU or 25-mg CCI-779 intravenous infusion weekly.

Eligibility for this study required histologically confirmed, advanced (stage IV or recurrent disease) RCC with no prior systemic therapy for the disease. Subjects with central nervous system metastases, prior anticancer therapy for RCC and prior investigational therapy/agents within 4 weeks of randomization were excluded from the study.

The primary objective of this study was efficacy with a primary endpoint of overall survival. Secondary objectives of this study were safety, health outcomes, and additional efficacy endpoints. The secondary efficacy endpoints of this study were an evaluation of progression-free survival, response rate (complete and partial responses), clinical benefit rate, the duration of overall response, time to treatment failure, and health outcomes measurements. In addition, subject responses across all 3 treatment arms were evaluated based on screening tumor expression of proteins involved in the AKT-mTOR pathway. Other planned and post-hoc analyses were performed to assess influence of tumor histology (clear cell vs. non-clear cell), age (65 years old vs. >/=65 years old), and prognostic-risk groups (intermediate vs. poor).

The following summarizes the results (Table 1) that were obtained:

TABLE 1

Overall Survival and Progression Free Survival in Phase III Study

| Tumor Histology | Clear-Cell | | Other | |
| --- | --- | --- | --- | --- |
| | αIFN | TEMSR | αIFN | TEMSR |
| Patients, n (%) | 170 (82) | 169 (82) | 36 (18) | 37 (18) |
| OS median, mo (95% CI) | 8.2 (6.6, 10.4) | 10.7 (8.5, 13.0) | 4.3 (3.2, 7.3) | 11.6 (8.9, 14.5) |
| OS HR, TEMSR:IFN (95% CI) | | 0.82 (0.64, 1.06) | | 0.49 (0.29, 0.85) |
| PFS median, mo (95% CI) | 3.7 (2.5, 4.6) | 5.5 (3.8, 7.1) | 1.8 (1.6, 2.1) | 7.0 (3.9, 8.9) |
| PFS HR, TEMSR:IFN (95% CI) | | 0.76 (0.60, 0.97) | | 0.38 (0.23, 0.62) |

The proportion of patients with different histologies was balanced across all arms of the study (81% clear-cell; 13% indeterminate; 6% non-clear cell). Of those with additional subtype data, 75% were papillary RCC. For patients with clear-cell tumors, median overall survival (OS) and progression-free survival (PFS) were longer for CCI-779 (TEMSR) vs. αIFN with hazard ratios (HR) of 0.82 and 0.76, respectively. For patients with other tumor histologies, median OS and PFS also were longer for TEMSR vs. αIFN with HR of 0.49 and 0.38, respectively. Among patients <65 years old, median OS and PFS were longer for TEMSR than for αIFN with HR of 0.62 and 0.61, respectively. There was no difference in OS or PFS for patients >/=65 years old treated with TEMSR or αIFN, but TEMSR had a better side effect profile than αIFN.

TEMSR prolonged PFS by 31% in patients with previously untreated clear-cell type, advanced renal cell carcinoma (advRCC)-with HR of 0.76 indicating that the risk of death or disease progression was reduced by 24%. TEMSR also improved OS by 22% in patients with previously untreated clear-cell advRCC vs. αIFN. A hazard ratio of 0.82 indicates an 18% reduction in risk of death for patients who received TEMSR as compared to αIFN.

TEMSR alone prolonged PFS by 163% in patients with previously untreated non clear-cell advRCC with a HR of 0.38 indicating that the risk of death or disease progression was reduced by 62%. TEMSR alone also improved OS by 104% in patients with previously untreated non clear-cell, advRCC vs.αIFN. A hazard ratio of 0.49 indicates a 51% reduction in risk of death for patients who received TEMSR as compared to αIFN.

In the population of patients <65yo, TEMSR prolonged PFS by 61% in patients with previously untreated advRCC. A hazard ratio of 0.62 indicates that the risk of death or disease progression was reduced by 38%. In the population of patients <65yo, TEMSR improved OS by 64% in patients with previously untreated advRCC vs. αIFN. A hazard ratio of 0.61 indicates a 39% reduction in risk of death for patients who received TEMSR as compared to αIFN.

All patents, patent applications, articles, and other documents referenced herein are incorporated by reference. It will be clear to one of skill in the art that modifications can be made to the specific embodiments described herein without departing from the scope of the invention.

The invention claimed is:

1. A method of treating papillary renal cell carcinoma in a mammal in need thereof, which comprises providing to said mammal an effective amount of CCI-779, wherein said papillary renal cell carcinoma is metastatic.

2. The method according to claim 1, wherein the papillary renal cell carcinoma is hereditary type I papillary renal cell carcinoma.

3. The method according to claim 1, wherein the papillary renal cell carcinoma is hereditary type II papillary renal cell carcinoma.

4. The method according to claim 1, wherein the papillary renal cell carcinoma is sporadic papillary renal cell carcinoma.

5. The method according to claim 1, wherein the papillary renal cell carcinoma is previously untreated papillary renal cell carcinoma.

6. The method according to claim 1, wherein the papillary renal cell carcinoma is advanced.

7. The method according to claim 1, wherein the CCI-779 is administered intravenously.

8. The method according to claim 1, wherein the CCI-779 is administered weekly for one to 24 months.

9. The method according to claim 1, wherein the CCI-779 is administered intravenously at a dose of 1 to 250 mg per week.

10. The method according to claim 9, wherein the CCI-779 is administered intravenously at a dose of 25 mg per week.

11. The method according to claim 1, wherein the CCI-779 is the sole anti-neoplastic agent in the regimen.

12. The method according to claim 1, wherein the CCI-779 is the sole active agent in the regimen.

13. The method according to claim 1, further comprising a further active agent, provided that the further active agent is not an interferon.

14. A method of treating papillary renal cell carcinoma in a mammal in need thereof, which comprises providing to said mammal an effective amount of CCI-779 in the absence of interferon alpha.

* * * * *